United States Patent [19]

Garner et al.

[11] Patent Number: 5,104,815
[45] Date of Patent: Apr. 14, 1992

[54] ASSAY FOR COBALAMINS

[75] Inventors: William D. Garner, Lake Bluff; Lynn M. Codacovi, Antioch; Phillip G. Mattingly, Grayslake; Christopher J. Welch, Urbana; Steven C. Kuemmerle, Grayslake, all of Ill.; Suzanne M. Delby, Kenosha, Wis.; Theresa L. Lane, Evanston, Ill.

[73] Assignee: Abbott Laboratories, Abbott Park, Ill.

[21] Appl. No.: 534,381

[22] Filed: Jun. 6, 1990

Related U.S. Application Data

[63] Continuation-in-part of Ser. No. 255,682, Oct. 11, 1988, abandoned.

[51] Int. Cl.$^5$ .............................................. G01N 33/82
[52] U.S. Cl. ........................................ 436/505; 435/4; 436/84
[58] Field of Search ....................... 435/4; 436/505, 84

[56] References Cited

PUBLICATIONS

Muir et al.—Brit. J. Haematology, vol. 53 (1983) pp. 423–435.

*Primary Examiner*—Sam Rosen
*Attorney, Agent, or Firm*—Richard D. Schmidt

[57] ABSTRACT

The current invention is a method, kit and reagents for detecting cobalamins in a sample. The method involves introducing into the sample a first conjugate of a latex or latex-like solid phase linked to affinity purified intrinsic factor with a first linking group at least three angstroms long. The first conjugate and the bound cobalamins in the sample are then exposed to a second conjugate of a cobalamin linked to a detectable enzyme to produce second conjugate bound to first conjugate and unbound second conjugate. The enzyme activity associated either with the solid phase first conjugate or the unbound second conjugate is then detected. By linking affinity purified intrinsic factor to a latex or latex-like solid phase with a first linking group at least three angstroms long, an exzyme assay can be performed which detects levels of cobalamins in patient samples within or below normal ranges found in such samples.

26 Claims, 2 Drawing Sheets

ASSAY FOR COBALAMINS

This is a continuation-in-part of copending application Ser. No. 07/255,682 filed on Oct. 11, 1988, now abandoned.

FIELD OF THE INVENTION

This application relates to a method and reagents for detecting the levels of cobalamins such as vitamin B12 in a sample, particularly an enzyme assay for detecting cobalamins.

DESCRIPTION OF RELATED ART

Cobalamins have the general structure shown below:

Cobalamins in the literature have in some instances been referred to generically as vitamin B12, but there are actually several different types of cobalamins which differ from each other by the R substituent shown in the structure above: cyanocobalamin (R=cyano), hydroxycobalamin (R=hydroxy), aquacobalamin (R=H$_2$O), nitritocobalamin (R=NO$_2$), 5' deoxyadenosylcobalamin (R=5' deoxyadenosyl), and methylcobalamin (R=methyl). Each of these cobalamins is considered generally to be a vitamin B12: cyanocobalamin (CN—Cbl; vitamin B12), hydroxycobalamin (OH—Cbl; vitamin B12a), aquacobalamin (Aq—Cbl; vitamin B12b), nitrocobalamin (NO—Cbl; vitamin B12c), 5' deoxyadenosylcobalamin (AdoCbl; coenzyme B12), methylcobalamin (MeCbl; methyl B12). The various cobalamins have similar metabolic activity. Cyanocobalamin, however, is more stable than the others.

The cobalamins are involved in many metabolic functions and are essential for normal growth and nutrition, hematopoiesis, production of all epithelial cells, and maintenance of mylelin throughout the nervous system. A deficiency in vitamin B12 manifests itself in ineffective hematopoiesis, inadequate mylelin synthesis, inadequate maintenance of the epithelial cells of the alimentary tract, and generalized anemia. Except for inadequate mylelin synthesis, however, these symptoms are common to many megaloblastic anemias, regardless of cause.

To pinpoint the cause of such anemias, it is necessary to test for vitamin B12 deficiencies. There are a variety of different assays for vitamin B12: colorometric, spectroscopic, fluorometric and radioactive isotope. The most common employs a cobalt 57 radioactive isotope in lieu of the cobalt in the corrin nucleus of the vitamin B12 molecule. The radioactively labelled molecule and B12 intrinsic factor are added to a sample containing B12, and the radioactively labelled B12 and the B12 in the sample compete for binding sites on B12 intrinsic factor. The B12 intrinsic factor is associated with a solid phase, so the amount of radioactivity on the solid phase or in the sample will be proportional to the amount of B12 in the original sample. The current radioassays have obvious disadvantages inasmuch as they involve the handling, storage, and disposal of radioactive materials. Furthermore, these methods require combined set up and assay times of about 2 hours.

Enzyme linked competitive binding assays have been proposed (see Bachas, *Biotechnics*, vol. 4, no. 1, p. 42 et seq. (1986)) for vitamin B12. However, the sensitivity of the assay was reported to be 1355 pg/ml while the normal range for vitamin B12 in human serum is from about 200-900 pg/ml. Clearly, such as assay cannot be used to test vitamin B12 deficiency since it reportedly cannot even detect vitamin B12 at normal ranges in human serum.

SUMMARY OF THE INVENTION

The current invention is a method, kit and reagents for detecting cobalamins in a sample. The method involves introducing into the sample a first conjugate of a solid phase linked to affinity purified intrinsic factor with a first linking group at least three angstroms long wherein the solid phase is a latex or latex-like material that contains surface primary amines or surface carboxyl groups. The first conjugate and the bound cobalamins from the sample are then exposed to a second conjugate of a cobalamin linked to a detectable enzyme to produce second conjugate bound to first conjugate and unbound second conjugate. The enzyme activity associated either with the solid phase first conjugate or the unbound second conjugate is then detected. By linking affinity purified intrinsic factor to a solid phase with a first linking group at least three angstroms long, an enzyme assay can be performed which detects levels of cobalamins in patient samples within or below normal ranges found in such samples.

In other aspects of this invention, the solid phase/intrinsic factor conjugate is first incubated with the sample, then the serum proteins are separated from the solid phase before the enzyme/cobalamin conjugate is added. This stepwise incubation, separation and second conjugate addition greatly improves assay sensitivity while keeping assay time to less than 1 hour.

The present invention also includes kits having the first and second conjugates described above. The present invention also includes assay methods and kits where the intrinsic factor is linked to the detectable enzyme, and where the cobalamin is linked to the solid phase.

DETAILED DESCRIPTION OF THE INVENTION

As indicated above, the current invention involves a method, kit, and reagents for determining cobalamins such as vitamin B12 in a sample which involves a conjugate of intrinsic factor with a latex or latex like solid phase having a linking group between them which is at least three angstroms in length. The use of this linking group is critical to the success of the current invention. The spacing of the intrinsic factor at least three angstroms from the surface of the solid phase, sufficiently counters the forces of attraction that the intrinsic factor and the solid phase exhibit toward each other. When using the latex or latex-like solid phase, materials of the present invention, it is critical that the intrinsic factor have sufficient space to capture the cobalamins. If the intrinsic factor is attached directly to the amine group carried by the solid phase, then the protein chain becomes entangled with, or at least inhibited by, the surface and it, therefore, has insufficient space to capture any cobalamin which may be present in the sample. By standing the intrinsic factor at least three angstroms away from the surface of the solid phase, the sensitivity of the enzymatic assay for B12, over radioisotope assays, can be increased greatly. By "increasing sensitivity" or "high sensitivity" is meant that lower concentrations of cobalamins can be detected. Assays according to this invention are capable of detecting cobalamins at concentrations less than 150 pg/ml and in many instances less than 100 pg/ml. In fact, the detection limit of an assay according to this invention has been found to be about 40 pg/ml.

The exact nature of the linking group does not appear to be critical provided it is at least three angstroms long, and preferably more than five angstroms long. Heterobifunctional linking groups such as those disclosed in U.S. patent application Ser. No. 114,930 filed Oct. 30, 1987 by Christopher Bieniarz et al., can be employed. Other linking groups can also beneficially be employed.

The intrinsic factor employed in the following examples is isolated from pig intestines by affinity chromotography. This is important because proteins which do not bind cobalamins, thereby reducing assay performance, will be excluded. In addition, it is important that the purified intrinsic factor have low R protein content. R proteins bind many porphyrin ring containing compounds, including cobalamins, so it is desirable to reduce their presence in the purified intrinsic factor used in an assay for cobalamins. Other sources of intrinsic factor can be from: mouse, cow or other mammals.

Suitable latex or latex-like solid phases employed in the present invention include sheets, plates, beads, fibers, filters, woven materials, and the like. Preferred solid phases are latex or latex-like microparticles which have primary amines attached, such as polymethylmethacrylate.

Preferably, the solid phase is in the form of small (0.1-1.0 um) microparticles containing either surface primary amines or surface carboxyl groups, as can be, obtained, for example, from Seradyn (Indianapolis, IN). The amine microparticles are used directly in the coupling procedure, but the carboxyl microparticles are converted to amines prior to coupling intrinsic factor.

Experiments suggest that the intrinsic factor on the solid phase has a "parking area" of between 30 and 400 angstroms$^2$/intrinsic factor molecule, and more preferably between 200 and 400 angstroms$^2$/intrinsic factor molecule. "Parking area" is the solid phase surface area per intrinsic factor molecule bound to the solid phase. With parking areas controlled, it is believed that the intrinsic factor molecules will not sterically hinder each other, when bound to the solid phase via linking groups which react with the reactive groups on the solid phase. Steric hindrance of intrinsic factor, it is believed, may affect its conformation, impairing its ability to bind with cobalamins.

It is also preferred that the cobalamin/enzyme conjugate employ a linking group between the enzyme and the cobalamin at least three angstroms in length, preferably about twenty angstroms in length. Preferably, the homobifunctional linking groups disclosed in Example 1 are employed. Other linking groups, however, are possible including the heterobifunctional groups of Examples 1, 7, and 8.

The detectable enzyme used in the cobalamin/enzyme conjugate can be any one of a variety of enzymes ordinarily used in enzyme assays, including alkaline phosphatase, horseradish peroxidase, beta galactosidase and the like. Alkaline phosphatase is preferred since it is well characterized, and many alkaline phosphatase substrates are stable when stored for long periods.

The preferred cobalamin for use in the enzyme/cobalamin conjugate is cyanocobalamin (CN—Cbl) itself. To attach it to an enzyme, however, CN—Cbl must be acid hydrolyzed to yield the carboxylate (compound 1, Example 1) at position 13 on ring C, which, is subsequently converted to an amine at the thirteenth position (Example 1, part c). The amine is then used to conjugate the enzyme to the B12 molecule. Other cobalamins can be used in this conjugate: vitamin B12a, vitamin B12b, vitamin B12c, coenzyme B12, and methyl B12 inasmuch as they bind to intrinsic factor. Other cobalamin derivatives (particularly those at position 13 on Ring C) can be employed and are considered cobalamins within the scope of this invention, as long as they can bind intrinsic factor.

In performing the assay of this invention, the intrinsic factor-solid phase conjugate is introduced into the sample to bind cobalamin in the sample. The remaining sample is washed from the solid phase, after which, a known amount of cobalamin-enzyme conjugate solution is passed over the solid phase to bind with any excess intrinsic factor on the solid phase. Either the enzyme activity associated with the solid phase, or that remaining in the excess cobalamin-enzyme conjugate solution can be assayed to determine the amount of cobalamin originally in the sample. Enzyme activity is assayed with a substrate for the enzyme, e.g. 4-methylumbelliferone phosphate if the enzyme is alkaline phosphatase.

As an alternative, the sample, latex or latex-like solid phase intrinsic factor and enzyme conjugate can be incubated together. Excess sample and enzyme conjugate are then washed away from the solid support, and indicator substrate is added.

The assay of this invention can be performed with kits provided with the appropriate reagents described above. Such kits include a first conjugate of affinity purified intrinsic factor linked to a latex or latex-like solid phase with a linking group at least three angstroms long. A second conjugate of a cobalamin and a detectable enzyme, preferably linked together with a linking group at least three angstroms long is also provided in the kit. The kit also includes a wash solution to wash the unbound first conjugate from the first conjugate bound to the second conjugate when the conjugates are used in the assay method described above. The kit also includes a substrate for the enzyme to detect enzyme activity.

The assay format above can be "reversed" by conjugating the cobalamin to the solid phase and the affinity purified intrinsic factor to the enzyme. In this configuration, the intrinsic factor/enzyme conjugate includes a linking group between the enzyme and the intrinsic factor at least three angstroms long. The colbalamin is linked to the latex or latex-like solid phase through a group on the C-ring of the cobalamin in a manner such that the cobalamin and the solid phase are spaced apart by at least a three angstrom length. This spacing can be accomplished by the use of a linker that may very depending upon the $B_{12}$ derivative used. In this reverse assay, the assay is performed by incubating the enzyme-intrinsic factor conjugate with the sample before adding the solid phase-B12 conjugate to the sample. The solid phase is then removed from solution and assayed for enzyme activity.

A number of examples follow which illustrate the invention, and are not intended to limit it. In Examples 1-8 B12 assays are described. In Example 9, the results of assays of Examples 1-6 are reported. In example 10, a relationship between sensitivity and parking area is shown.

EXAMPLE 1

Assay for B12 Using an Enzyme B12 Conjugate Having a 23 Atom Linker, and a Solid Phase-Intrinsic Factor Conjugate Having a 18 Atom Linker

A. Preparation of B12 Derivative i) General Procedure

In this procedure, cyanocobalamin was acid hydrolyzed with 0.8 M phosphoric acid to a mixture of carboxylic acids, of which the monocarboxylic acids were isolated. The acid was then coupled to 1,6 diamino hexane to give a B12 amine.

ii) Acid Hydrolysis

Vitamin B12 (2.2 g) was put into 0.8 M phosphoric acid (300 ml) and heated to 70° C. for six hours under nitrogen in the dark. The B12 reaction mixture was desalted over Amberlite XAD-2. The washed resin was packed in 4×60 cm column. The reaction mixture was applied to the column and unbound derivatives were eluted. The bound B12 acids were eluted with methanol and concentrated by rotary evaporation.

iii) Purification

The individual B12 acids were separated on DE-52 Cellulose column (washed with NaOH, HCL, NaOAc, then equilibrated to pH 5.0 with water). A 4×75 cm column was prepared, and the sample was added and slowly eluted. After two days, a single red band containing unreactive corinoid was removed with distilled water. The B12 monoacids were eluted with 0.05% acetic acid. Three peaks were eluted in 1.5 days. Each band was collected and concentrated by rotary evaporation. Only fractions containing red material were pooled (orange-yellow fractions were discarded). The red fractions were tested for B12 reactivity in a radioassay. The B12 monoacids were characterized by mass spec, c13 NMR, and HPLC. The thirteenth position (i.e., position 13 on ring c), carboxylated B12 (Compound 1) was produced.

COMPOUND 1 iv) Conversion of Carboxyl to Amine

Compound 1 (63 mg; 45 uM) and 1,6 hexyldiamine (0.2554 g; 2.2 mM) were dissolved in distilled water (13 ml). The pH of the solution was adjusted to 6.0 with 1N HCl. 1-Ethyl-3-(3-dimethylaminopropyl)-carbodiimide (EDAC) (88.8 mg; 463 uM) was added, and the solution was stirred overnight under nitrogen (Tetsuo Toraya, *J. Biol. Chem.*, 255:3520 3525 (1980)). The reaction was concentrated by rotary evaporation and purified by HPLC (Tetsuo Toraya, *Biochem.*, 18:417 426 (1979)). The B12 was purified on a C-18 (Magnum 9) column using 20/80 (methanol/1% acetic acid) solvent system at a flow rate of 4 ml/min (after 80 minutes flow was increased to 6 ml/min.). The amine was characterized by mass spec and HPLC. These chemistries provided the following B12 -amine (Compound 2) which was used to make an enzyme conjugate in Example 1 part F.

B. Purification of Intrinsic Factor From Pig Intestine 1.5-2.5 kg pig duodemum were washed and cut into small pieces. The pieces were blended, acidified with perchloric acid to pH 1.0, and mixed for one hour. The coarse solids were removed by centrifugation, and the supernatant was neutralized with KOH (5N) and $K_2HPO_4$. On storage overnight at 4° C., a precipitate was formed. The top 90% of the supernatant was decanted, $SiO_2$ was added and the solution centrifuged. The clarified supernatant was filtered through celite to remove lipid. The intrinsic factor in the clear filtrate was purified by affinity chromatography, in the presence of cobinamide on a column having a B12 derivative ligated to agarose.

The non specifically bound protein was removed by washing the column sequentially with 4 M NaCl, glucine/sodium sucrose and 50 mM potassium phosphate buffer. The intrinsic factor was eluted with 3.8 M

COMPOUND 2

Guanidine-HCl. The intrinsic factor in the desired fractions was tested for the presence of R proteins which bind many porphorine ring-containing compounds (i.e. cobinamides) including but not limited to cobalamins. Once the intrinsic factor was tested (by radioassay using B12 cobalt 57) to contain less than 0.004% cross reactivity with cobinamides, the intrinsic factor was exhaustively dialyzed with several changes of deionized water. The first fraction, affinity purified in this manner, has been found to contain proteins of which at least 95% bind cobalamins, yielding NLT 2000 ng B12 binding/ml (2000 Units). Less than about 95% functional purity was found to yield assays with impaired sensitivity.

functional linker of about 29.1 angstroms in length, as a white solid with 48% overall yield.

COMPOUND 4

C. Preparation of 23 Atom Linker i. Synthesis of Compound 3

The extended length heterobifunctional linkers were synthesized as described in U.S. patent application Ser. No. 114,930 which is incorporated herein by reference. Trans-4-(amino methyl) cyclohexanecarboxylic acid (Aldrich Chemical Co.) was converted to N-(4-carboxycyclohexylmethyl) maleimide by the method of Yoshitake (J. Biochem., 101:395-399 (1979)). This material (100 mg) was then dissolved in dry dimethyl formamide (DMF) (1.0 ml), 6-aminocaproic acid (39.2 mg; 1.0 eq) was added, and the resulting mixture was stirred overnight at room temperature under nitrogen atmosphere. The following morning, dicyclohexylcarbodiimide (DCCI) (67.8 mg; 1.1 eq) was added, and the reaction mixture was stirred for an additional six hours. Precipitated dicyclohexylurea (DCU) was removed by filtration, and the resulting DMF solution was evaporated under reduced pressure to give a tacky solid, which was purified by flash chromatography upon silica gel (5% methanol/chloroform) to yield Compound 3 (71 mg) as a white solid with 53% overall yield.

ii. Synthesis of 23 Atom Heterobifunctional Linker

Compound 3 (100 mg; synthesis described above) was dissolved in dry DMF (1.0 ml), 6 aminocaproic acid (29.3 mg; 1.0 eq) was added, and the resulting mixture was stirred overnight at room temperature under nitrogen atmosphere. The following morning, DCCI (50.7 mg; 1.1 eq) was added, and the reaction mixture was stirred for an additional six hours. Solid precipitate (DCU) was removed by filtration and the resulting DMF solution was evaporated under reduced pressure to to give a tacky solid, which was purified by flash chromatography upon silica gel (10% methanol/chloroform) to give compound 4 (60 mg), a heterobifunctional linker of about 29.1 angstroms in length, as a white solid with 48% overall yield.

D. Coupling of Intrinsic Factor to Amine Microparticles Using 23 Atom Linker i. Washing Microparticles

Biorad Bio-Rex MSX 501 (D) resin (189) was washed with 2 L of deionized water. Amino microparticles (Seradyn, 0.485 um average diameter) were added to the resin which was mixed with deionized water, and the mixture was rotated for one hour at room temperature. The resin was allowed to settle, and the microparticles decanted. Deionized water (1.0 ml/0.5 gr resin) was added to the resin, the resin was mixed, and allowed to settle. Microparticles were once again decanted from the resin. The water rinse/mix/decant procedure was repeated twice. The microparticle preparation obtained was adjusted to 12-17 percent solids with the addition of deinionized water.

ii. Preparation of Microparticles/Intrinsic Factor Conjugate

Equal volumes of washed microparticles and 0.1% DTAB were mixed for 15 minutes at room temperature. The particles were recovered and resuspended in H2O to give 7.5% solids. Microparticles, (0.6%), intrinsic factor (700 u) and compound 4 (80 uM) were combined in 17.5 mM TEA butter (pH 8.0) in a total volume of 1.0 ml. This solution was mixed for 2 hours in the dark room temperature. After incubation, the particles were pelletted and washed several times in mild detergent/50 mM TRIS buffer, homogenized to ensure uniform particle size distribution, and diluted to the desired concentration.

E. Preparation of 18 Atom Homobifunctional Linker i. Synthesis of 4 Atom Homobifunctional Linker

COMPOUND 3

N hydroxysuccinimide (8.16 g) was dissolved in dry dimethylformamide (DMF, 200 ML) with triethylamine (7.17 g). Succinyl chloride (5.0 g) was added slowly via addition funnel to the stirring reaction mixture under nitrogen atmosphere. The mixture was stirred for eight hours at room temperature. The precipitate was removed by filtration, and dried under high vacuum to give crude product, which was then triturated with chloroform (50 ml) and argon-dried under high vacuum to give 8.52 g (85%) of pure white powder Compound

5—a homobifunctional linker of about 20.3 angstroms in length.

COMPOUND 5 ii. Synthesis of 18 Atom Homobifunctional Linker

Compound 5 (5.0 g) was dissolved in dry DMF (150 ml), 6-aminocaproic acid (4.20 g) was added, and the reaction mixture was stirred for three hours at room temperature under a nitrogen atmosphere. Dicyclohexylcarbodiimide (DCCI, 6.93 g) was then added and mixed overnight. The following morning dicyclohexyl urea (DCU) precipitate was removed by filtration, and the resulting DMF solution was evaporated under reduced pressure to give a tacky solid. Trituration with ether followed by drying under high vacuum yields 7.94 g pure product (92% yield), Compound 6, a homobifunctional linker of about 38 angstroms in length.

COMPOUND 6

F. Conjugation of B12 Amine Derivative to Alkaline Phosphatase With 18 Atom Homobifunctional Linker Alkaline phosphatase (Boehringer Mannheim; 10 mg/ml) was dialyzed in potassium phosphate buffer (50 mM, pH 7.4) containing 0.1 mM zinc chloride.

The B12 amine (Compound 2, 0.173 ml, 0.82 mM in 50:50 v/v DMF/DMSO), the 18 atom homobifunctional reagent (Compound 5, 1.142 ml, 1.88 mM in 50:50 (v/v) DMF/DMSO) and 50:50 DMF/DMSO (0.0749 ml) were placed in a glass vial and allowed to react for thirty minutes at room temperature. The B12 solution (1.0 ml) was added to the dialyzed alkaline phosphatase (1.0 ml), mixed gently, and allowed to stand for 16–24 hours at 4° C. The mixture was separated on Sephadex G 50-100 (1.2×44 cm) using 50 mM Tris pH 7.4 containing 1.0 mM magnesium chloride and 0.10 mM zinc chloride (Tris/Mg/Zn). The appropriate fractions were pooled and dialyzed against 1000 ml Tris/Mg/Zn to yield B12/alkaline phosphatase conjugate linked with an 18 atom linker.

G. Assay Performance

With the enzyme-B12 conjugate of part F and the solid phase-intrinsic factor conjugate of part D, an enzyme linked assay was performed on a fully automated machine (ABBOTT IMx analyzer) as described below.

i. Standards

Figure 1:
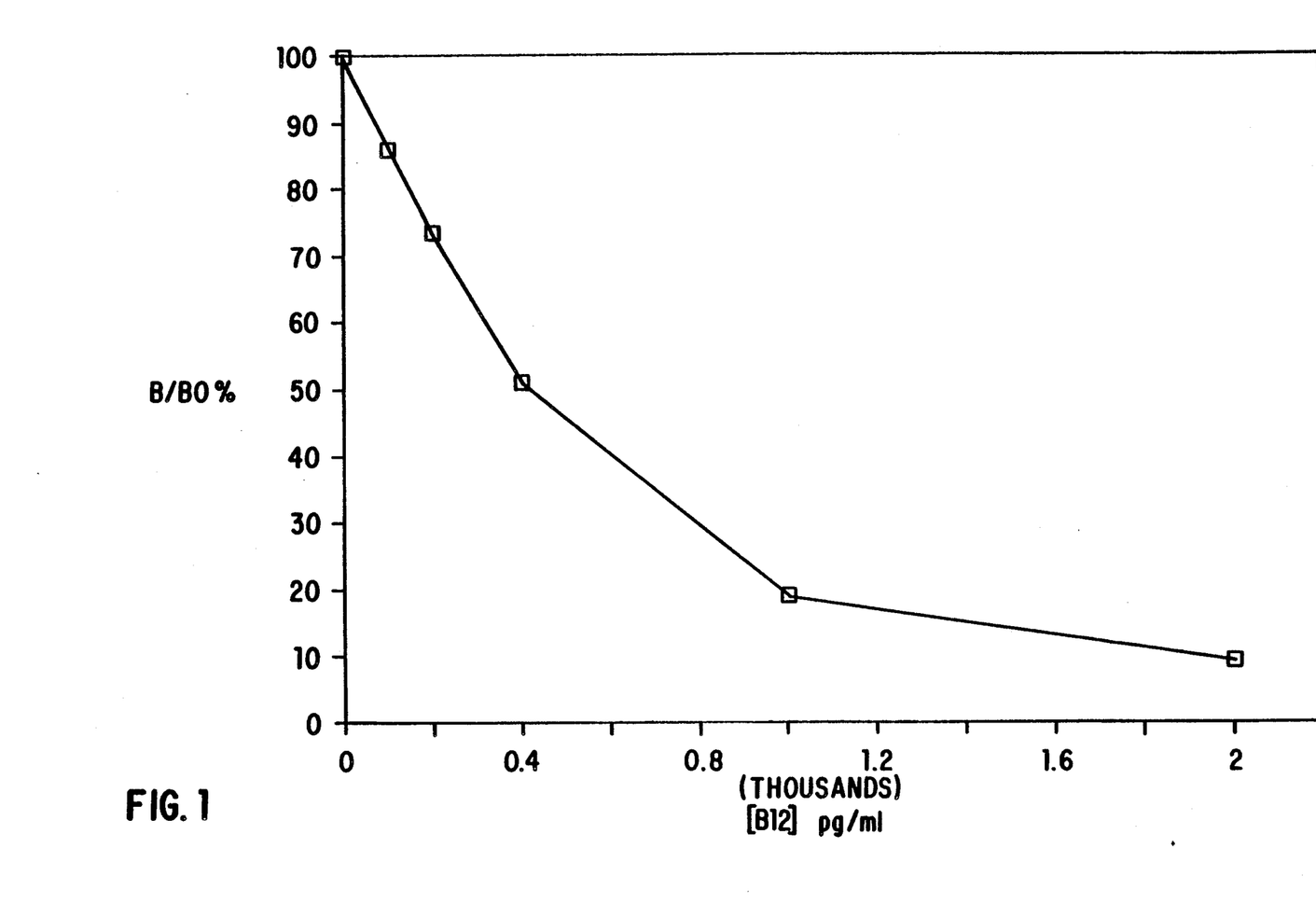
FIG. 1 is a calibration curve obtained when performing the assay of this invention on an Abbott Laboratories IMx® analyzer.

Solutions used to generate the standard curve of FIG. 1 were prepared by dilutions of USP cyanocobalamine standard in sodium borate (10 mM, pH 7.5), containing 2% HSA, 0.15 N NaCl, and 0.1% $NaN_3$. The following dilutions were prepared: 0, 100, 200, 400, 1000, and 2000 pg/ml standards.

ii. Enzyme-B12 Conjugate Solution

The enzyme-B12 conjugate of part F was diluted 1:200 in conjugate diluent: Tris (50 mM, pH 7.4) containing 1% BSA, 100 mM NaCl, 1.0 mM $MgCl_2$, 0.1 mM ZnCl, and 0.1% $NaN_3$.

iii. Intrinsic Factor-Microparticle Conjugate Solution

The solid phase-intrinsic factor conjugate of part D was diluted 1:1000 in particle diluent: borate (0.05 M, pH 7.25 containing 1% BSA, 0.4 M sucrose, 0.1% $NaN_3$, 0.01% Tween 20.

iv. Alkaline Phosphatase Substrate Indicator

A fluorescence indicator reagent was prepared: 100 mM 2-amino-2-methyl-1-propanol (AMP) pH 10.3 containing 1 mM magnesium chloride, 4 mM tetramisole, 1.2 mM 4-methylumbelliferone-phosphate (MUP), and 0.1% sodium azide. MUP was hydrolized by alkaline phosphatase, liberating inorganic phosphate and 4-methylumbelliferone (MU) which fluoresces: excitation and emission were 362 and 448 nm, respectively. The generation of MU over time is the rate read illustrated in FIG. 1 measured immediately after addition of MUP to the reaction mixture.

v. Assay Protocol and Separation Method

A volume of standard or sample is combined with NaOH (0.4 N), cobinamide (250 ng/ml), KCN (0.001%) and a thiol reagent (e.g. x-monothiogycerol, B mercaptoethanol, dithiotheitol etc.) at 34° C. for 8 minutes. This treatment forces the dissociation of serum B12 from endogenous binding proteins and convert all vitamin B12 forms to cyanocobalamin. Other sample treatment alternatives include: 1) boiling sample diluted into buffer containing a thiol agent, HSA (0.1–0.5%) and KCN (0.001%) or 2) adding perchloric acid (65%) to sample to precipitate serum proteins. Sample is then centrifuged, and the clear supernatant is further assayed for B12 content.

The denatured solution was neutralized with microparticle intrinsic factor conjugate solution and incubated for fifteen minutes. Then the sample microparticle preparation was deposited on a filter surface (an $IM_x$ disposable reaction cell sold by Abbott Laboratories, North Chicago, Ill.) to separate microparticle bound from free B12. After a wash with 50 mM Tris pH 7.4 (a wash solution), the B12 alkaline phosphatase conjugate solution (50 ul) was added to the filter surface to bind free intrinsic factor sites. The filter was washed and alkaline phosphatase substrate reagent was added. The IMx analyzer read the rate of substrate conversion to fluorescent product and calculated sample B12 concentration based on standard curve values.

The resulting assay demonstrated a sensitivity of less than 60 pg/ml based on a calculation using two times the standard deviation (SD) of multiple runs of the zero standard and reading the 2SD's off the curve as a sample.

vi. Patient Correlation Abbott B12 IMx Assay Vs Becton Dickinson B12 RIA

Figure 2:
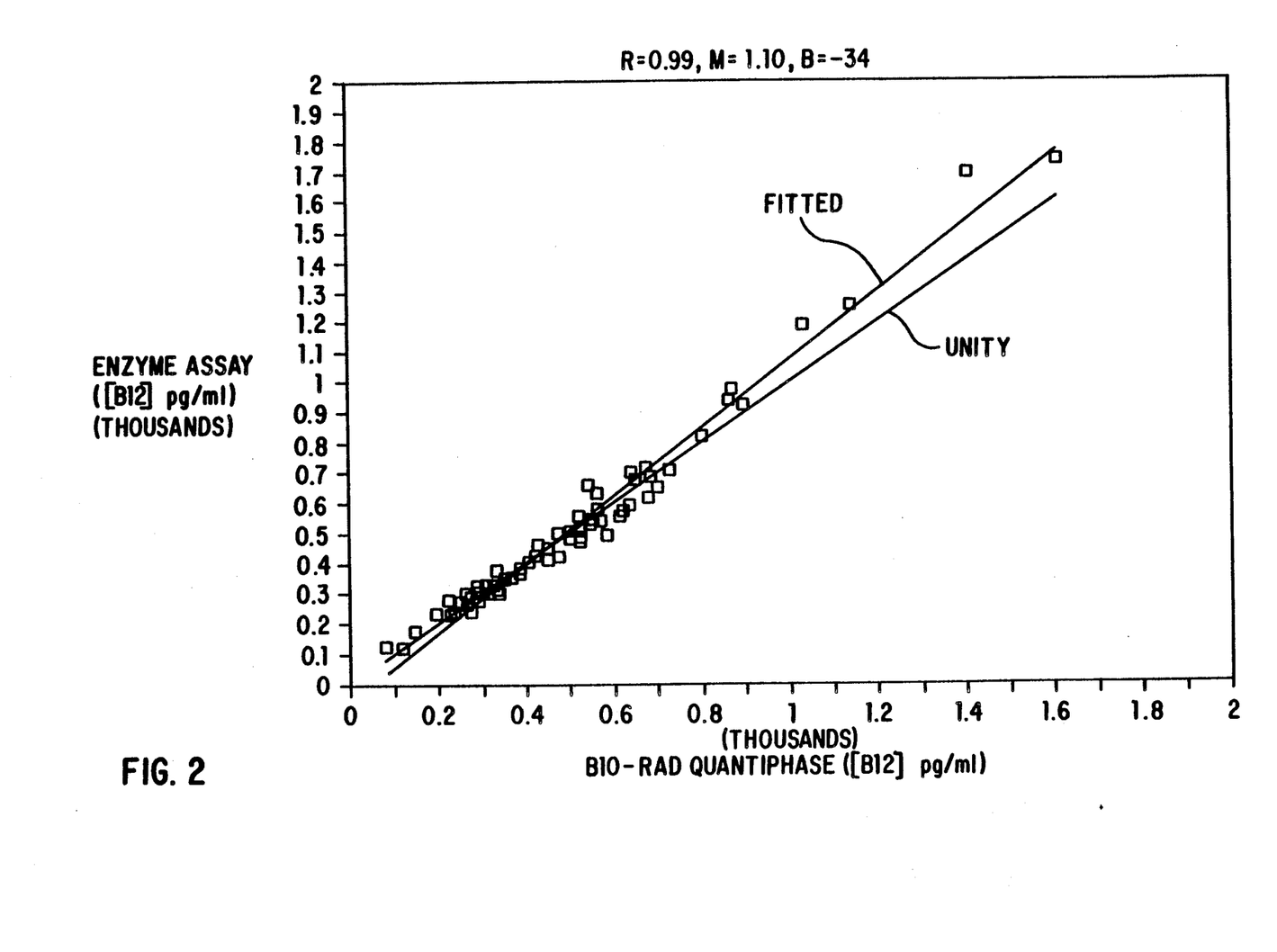
FIG. 2 is a correlation between the assay of this invention and a commercially available radioisotope assay.

Patient serum samples (n=76) were tested in the Abbott IMx analyzer using the enzyme assay of this invention and in the commercially available BIORAD, Quantaphase ™ radioassay. The correlation plot of FIG. 2 was calculated. The slope was 1.10, and the correlation coefficient (R) was 0.99.

EXAMPLE 2

Assay for B12 Using an Enzyme-B12 Conjugate Having a 18 Atom Linker, and a Solid Phase-Intrinsic Factor Conjugate Without a Linker A. Assay performance An assay was performed following the procedure and using the reagents described in Example 1, except that an intrinsic factor/microparticle conjugate without a linker group was used instead of the conjugate described in Example 1, part D (ii). The synthesis of intrinsic factor/microparticle conjugate without a linker group is described in part B below.

B. Conjugation of Intrinsic Factor To Microparticles Without a Linker Group

EDAC solution (0.34 ml, 0.2 M EDAC in 0.1 M 2-(N-morpholine)ethanesulfonic acid) was mixed with 2 percent carboxy microparticle solution (0.34 ml) from Example 7, part A (i). The mixture was sonicated to disperse it, and rotated end-over end for one hour at 25° C. The mixture was centrifuged, and the pellet was washed with 0.1 M 2(N-morpholine)ethanesulfonic acid (MES) pH 7.0. The mixture (containing EDAC activated microparticles) was centrifuged, and the pellet suspended in deionized water (0.28 ml).

The EDAC activated microparticles (280 ul) and intrinsic factor (280 ul; 38 ug/ml) from Example 10 were placed in a small plastic vial. The mixture was rotated overnight at 25° C., washed twice with 0.05 percent Tween 20 in deionized water, and washed twice with 0.05 M Tris buffer, pH 7.4. An intrinsic factor/microparticle conjugate with the intrinsic factor directly conjugated to the microparticle was produced.

EXAMPLE 3

Assay for B12 Using an Enzyme-B12 Conjugate Having a 18 Atom Linker, and a Solid Phase Intrinsic Factor Conjugate Having a 4 Atom Linker A. Assay performance An assay was performed following the procedure and using the reagents described in Example 1, except that an intrinsic factor/microparticle conjugate with a four atom linker group was used instead of the conjugate described in Example 1, part D (ii). The synthesis of intrinsic factor/microparticle conjugate with a four atom linker group was described in part B below.

B. Coupling Intrinsic Factor to Amine Microparticles Using 4 Atom Linker

The procedure of Example 1 part D was repeated, substituting Compound 5 for Compound 4 in Example 1 part D, and modifying the procedure as follows. The homobifunctional linker Compound 5 was incubated with the amine microparticles for one half hour, then intrinsic factor was added with buffer. The mixture was rotated overnight at 25° C., and treated thereafter as described in Example 1 part D (ii) to produce the captioned conjugate.

EXAMPLE 4

Assay for B12 Using an Enzyme-B12 Conjugate Having a 18 Atom Linker, and a Solid Phase-Intrinsic Factor Conjugate Having a 9 Atom Linker A. Assay performance An assay was performed following the procedure and using the reagents described in Example 1, except that an intrinsic factor/microparticle conjugate with a nine atom linker group was used instead of the conjugate described in Example 1, part D. The synthesis of intrinsic factor/microparticle conjugate with a nine atom linker group is described in part B below.

B. Coupling Intrinsic Factor to Amine Microparticles Using 9 Atom Linker

The procedure of Example 1 part E was repeated substituting succinimidyl-4-(N-maleimidomethyl) cyclohexane-1-carboxylate (SMCC) for Compound 4 in Example 1, part C to produce the captioned product.

EXAMPLE 5

Assay for B12 Using an Enzyme-B12 Conjugate Having a 18 Atom Linker, and a Solid Phase-Intrinsic Factor Conjugate Having a 16 Atom Linker A. Assay performance An assay was performed with the procedure and the reagents described in Example 1, except that an intrinsic factor/microparticle conjugate with a sixteen atom linker group was used instead of the conjugate described in Example 1, part D. The synthesis of intrinsic factor/microparticle conjugate with a sixteen atom linker group is described in part B below.

B. Coupling Intrinsic Factor to Amine Microparticles Using 16 Atom Linker

The procedure of Example 1 part D was repeated substituting Compound 3 for Compound 4 in Example 1, part C to produce the captioned product.

EXAMPLE 6

Assay for B12 Using an Enzyme B12 Conjugate Having a 18 Atom Linker, and a Solid Phase-Intrinsic Factor Conjugate Having a 30 Atom Linker A. Assay performance

An assay was performed with the procedure and the reagents described in Example 1, except that an intrinsic factor/microparticle conjugate with a 30 atom linker group was used instead of the conjugate described in Example 1, part D (ii). The synthesis of intrinsic factor/microparticle conjugate with a 30 atom linker group is described in part C below.

B. Synthesis of 30 Atom Heterobifunctional Linker

Compound 4 (100 mg; synthesis above) was dissolved in dry DMF (2.0 ml), 6-aminocaproic acid (23.4 mg; 1.0 eq) was added, and the resulting mixture was stirred overnight at room temperature under nitrogen atmosphere. The following morning, DCCI (40.5 mg; 1.1 eq) was added, and the reaction mixture was stirred for an additional six hours. Solid precipitate (DCU) was removed by filtration and the resulting DMF solution was evaporated under reduced pressure to give a tacky solid, which was purified by flash chromatography upon silica gel (10% methanol/chloroform) to give Compound 7 (60.0 mg), a heterobifunctional linker of about 38 angstroms in length, as a white solid with 50% overall yield.

2.5 percent solids, and resin was added (0.5 g resin/ml of microparticles). The mixture was rotated one hour at room temperature. The resin was settled, and microparticles decanted. The resin was washed several times; each time microparticles were decanted. Alternatively,

COMPOUND 7

C. Coupling Intrinsic Factor to Amine Microparticles Using 30 Atom Linker

The procedure of Example 1 part D was repeated substituting Compound 7 for Compound 4 in Example 1, part D (ii) to produce the captioned product.

EXAMPLE 7

Other Cobalamin Assays

Other cobalamin assays can be performed with the solid phase-intrinsic factor conjugates described in parts A to G below.

A. Synthesis of Intrinsic Factor Solid Phase Conjugate with 36 Atom Linker.

i. Synthesis of 36 Atom Heterobifunctional Linker

Compound 7 (100 mg; synthesis described above) was dissolved in dry DMF (10.0 ml), 6-aminocaproic acid (19.5 mg; 1.0 eq) was added, and the resulting mixture was stirred overnight at room temperature under nitrogen atmosphere. The following morning, DCCI (33.7 mg; 1.1 eq) was added, and the reaction mixture was stirred for an additional six hours. Solid precipitate (DCU) was removed by filtration, and the resulting DMF solution was evaporated under reduced pressure to give a tacky solid, which was purified by flash chromatography upon silica gel (10% methanol/chloroform) to give Compound 8 (53 mg), a heterobifunctional linker of about 48 angstroms in length, as a white solid with 45% overall yield.

the remaining microparticles can be filtered from the resin with a sintered glass funnel, and washed with deionized water. The microparticles were centrifuged, and the pellet resuspended to 2% solids (w/v) in 0.1 M 2-(N morpholine)ethane sulfonic acid (MES), pH 5.0.

ii. Conversion of Carboxy to Amine Microparticles

EDAC solution (5 ml, 0.2 M EDAC in 0.1 M MES (pH 5.0) was mixed with 2 percent microparticle solution (5 ml) from Example 7, part B (i). The mixture was sonicated to disperse it, and rotated end over-end for one hour at 25° C. The mixture was centrifuged, and the pellet was washed with 0.1 M MES pH 5.0. The mixture was centrifuged, and the pellet suspended in 0.05 M Tris-HCl pH 7.6 (5.0 ml). To the EDAC-activated microparticles (5.0 ml). 0.4 M ethylene diamine (5 ml) in 0.05 M Tris HCl, pH 7.6 was added, and the mixture was rotated end-over-end overnight at 25° C. The mixture was centrifuged, and the pellet was washed with 0.05 M Tris-HCl pH 7.6. The amine particles were then centrifuged, and the pellet was resuspended in deionized water to yield 13 percent (v/v) amine particles.

iii. Preparation of Microparticle/Intrinsic Factor Conjugate

The microparticles from part b (300 ul), intrinsic factor (600 ul; 38 ug/ml) from Example 1 part B, and Compound 4 (33 ul; 1.0 mg/ml in DMF) were placed in a small plastic vial. The mixture was rotated overnight at 25° C., washed twice with 0.05 percent Tween 20 in deionized water, and washed twice with 0.05 M Tris pH 7.4. The intrinsic factor/microparticle conjugate with

COMPOUND 8 ii. Coupling Intrinsic Factor to Amine Microparticles Using 36 Atom Linker

The procedure of Example 1 part D was repeated substituting Compound 8 for Compound 4 in Example 1, part D (ii) to produce the captioned conjugate.

B. Coupling of Intrinsic Factor to Carboxyl Microparticles Using 23 Atom Linker i. Washing Microparticles Biorad Bio Rex MSZ 501 (D) resin was washed several times with deionized water. Carboxylated modified microparticles (Seradyn, 5-15% solids) were diluted to the 23 atom linker was produced.

C. Coupling of Intrinsic Factor to Carboxyl Microparticles Using 36 Atom Linker The process of Example 7 part B was repeated substituting Compound 8 for Compound 4 in Example 7, part B (iii) to produce the captioned conjugate.

D. Coupling of Intrinsic Factor to Carboxyl Microparticles Using 4 Atom Homobifunctional Linker The procedures of Example 7, parts B (i) and (ii) were repeated. The process of Example 7, part B (iii) was repeated substituting the homobifunctional linker Compound 5 for Compound 4, and modifying the process of Example 7, part B (iii) as follows: the microparticles and Compound 5 were rotated for one half hour, then the intrinsic factor was added with buffer. The mixture was rotated overnight at 25° C., and washed as described in Example 7, part B (iii) to produce the captioned conjugate.

E. Coupling of Intrinsic Factor to Carboxyl Microparticles Using 18 Atom Homobifunctional Linker The procedures of Example 7, parts B (i) and (ii) were repeated. The process of Example 7, part B (iii) was repeated substituting the homobifunctional linker Compound 6 for Compound 4, and modifying the process of Example 7, part B (iii) as follows:. the microparticles and Compound 6 were rotated for one half hour, then the intrinsic factor was added with buffer. The mixture was rotated overnight at 25° C., and washed as described in Example 7, part B (iii) to produce the captioned conjugate.

F. Coupling of Intrinsic Factor Via Avidin-Biotin to Solid Phase i. Preparation of Solid Phase The carboxylated microparticles were washed as described in Example 7, part B (i), and converted to amine microparticles according to the procedure of part ii below.

ii. Attachment of Poly-1-lysine to Carboxyl Microparticles

The microparticles (200 ul) from above, poly-1-lysine (4000–6000 molecular weight; 50 ul, 2.5 mg/ml in potassium phosphate buffer), potassium phosphate buffer (400 ul; 50 mM) and EDAC were placed in a microfuge tube, incubated for two hours at 25° C. and centrifuged. The pellet (which included microparticles conjugated to poly-1-lysine) was washed twice with potassium phosphate buffer, and resuspended in deionized water (500 ul).

iii. Coupling of Avidin to Poly-1-lysine Microparticles

In a glass container, bovine gamma globulin (4.25 mg, Sigma), avidin (6.225 mg), phosphate buffer (pH 7.2, 9 ml) were mixed until all ingredients were dissolved. In a separate glass container, freshly prepared glutaraldehyde (36 ul) and phosphate buffer (9 ml) were mixed well. The avidin and glutaraldehyde solutions were then mixed together, and placed on a shaker for sixty minutes at 25° C. Then the mixture was placed on a rotator for two hours at 2°–8° C.

The poly-1-lysine microparticles were washed with phosphate buffer, and the microparticles (280 ul) were mixed with the avidin-glutaraldehyde preparation (18 ml). The mixture was then rotated for two hours at 2°–8° C. The reaction mixture was centrifuged and washed three times. The pellets were resuspended with a syringe. The particles produced were microparticle-avidin conjugates.

iv. Biotin Intrinsic Factor Conjugates

Biotin LC-NHS (Pierce Co.) was dissolved in DMF (150 ul), then intrinsic factor solution (3 ml) from Example 1 and borate buffer pH 8.5 (300 ul) were added to the biotin in a molar ratio of 100:1 biotin to intrinsic factor. The mixture was mixed well, but slowly, and allowed to react overnight at 2°–8° C. The solution was dialyzed exhaustively in deionized water with 12–14,000 mw tubing. The product produced was biotin-intrinsic factor conjugate.

v. Intrinsic Factor/Microparticle Conjugate

The avidin/microparticle conjugate (1 ml) from part iii, biotin intrinsic factor conjugate (100 ul) from part iv, and phosphate buffer (250 ul) were mixed together in a vial and rotated overnight at 2°–8° C. The reaction mixture was then centrifuged and washed two times with 0.05 M Tris pH 7.4. The conjugate produced was intrinsic factor linked to microparticles with a biotin avidin.

G. Coupling Intrinsic Factor to Amine Microparticles Using 18 Atom Linker

The procedure of Example 1 part D was repeated substituting Compound 6 for Compound 4 in Example 1, part D (ii), modifying the procedure as follows. The homobifunctional linker Compound 6 was incubated with the amine microparticles for one-half hour, then intrinsic factor was added with buffer. The mixture was rotated overnight at 25° C., and treated thereafter as described in Example 1, part D (ii) to produce the captioned conjugate.

EXAMPLE 8

Assay Using B12/Alkaline Phosphatase Conjugate With EDAC Linking Reagent

A. Assay performance

An assay was performed using enzyme B12 conjugates different from the conjugate in Example 1 part F. Specifically, an assay was performed following the procedure set forth in Example 1, except with a B12/alkaline phosphatase conjugate with an EDAC linking reagent (synthesis described below) instead of the conjugate of Example 1, part F.

B. Synthesis of B12/Alkaline Phosphatase Conjugate With EDAC Linking Reagent

EDAC (1 mg), Compound 1 (0.1 ml, 2.3 mM in 50:50 (v/v) DMF/DMSO), and N hydroxysuccinimide (0.009 ml, 20 mM in DMF) were placed into a vial and allowed to react at room temperature for two hours. The reaction mixture volume was increased to 1.0 ml with 50:50 (v/v) DMF/DMSO. The EDAC activated B12 was added to alkaline phosphatase (1.0 ml, 10 mg/ml in 50 mM potassium phosphate, 0.1 mM ZnCl solution), and the mixture was allowed to stand for 16–24 hours at 4° C. The B12 alkaline phosphatase conjugate was purified as described in Example 1 part F above.

EXAMPLE 9

Intrinsic Factor Linker-Microparticle System vs Sensitivity

The sensitivity of an assay using intrinsic factor-linker-microparticles produced with linkers of varied length was studied. In each instance, the sensitivity was tested using the B12-enzyme conjugate of Example 1 with the assay protocol outlined previously in Example 1.

TABLE I

| Solid Phase Conjugate | Distance (Angstroms) | Sensitivity (pg/ml) | Linker Length (Atoms) |
|---|---|---|---|
| Example 2 | 2.6 | 227 | 0 |
| Example 3 | 6.4 | 36 | 4 |
| Example 4 | 11.4 | 51 | 9 |

TABLE I-continued

| Solid Phase Conjugate | Distance (Angstroms) | Sensitivity (pg/ml) | Linker Length (Atoms) |
|---|---|---|---|
| Example 5 | 20.3 | 50 | 16 |
| Example 1 | 29.1 | 48 | 23 |
| Example 6 | 37.9 | 40 | 30 |

EXAMPLE 10

Parking Area-Sensitivity Relationship

A relationship between parking area and sensitivity was shown by synthesizing intrinsic factor-solid phase conjugates using solid phases having reactive group parking areas of various values, and conducting the reactions which generate the conjugates so that as many reactive groups as possible were linked to intrinsic factor molecules. Thus, the reactive group parking area and the intrinsic factor parking area can be assumed to be quite similar. Specifically, carboxyl microparticles having various reactive group parking areas provided by the manufacturer (Seradyn, Indianapolis, Ind.) were derivativitized to amine microparticles as described previously, and linked via heterobifunctional linking groups to intrinsic factor. The relationship of the reactive group parking area (and presumably the intrinsic factor parking area) to the assay sensitivity (as determined using the standard deviation calculations of Example 1) was set forth in Table II below.

TABLE II

| Parking Area-Sensitivity Relationship | |
|---|---|
| Parking Area | Sensitivity |
| 60 Angstrom$^2$/RG | 100 pg/ml |
| 154 Angstrom$^2$/RG | 60 pg/ml |
| 283 Angstrom$^2$/RG | 35 pg/ml |
| 390 Angstrom$^2$/RG | 30 pg/ml |

(RG = reactive group)

While several embodiments of this invention have been described, others will become apparent to those of ordinary skill in the art. Such embodiments are within the scope of this invention, unless the claims which follow expressly state otherwise.

What is claimed is:

1. A method for detecting cobalamins in a sample, comprising:
   a) combining into the sample a first conjugate of a latex solid phase linked to affinity purified intrinsic factor with a first linking group at least three angstroms long and interposed between said solid phase and said intrinsic factor wherein said solid phase contains surface primary amine groups or surface primary carboxyl groups;
   b) exposing said first conjugate and cobalamins to a second conjugate of a cobalamin linked to a detectable enzyme to produce second conjugate bound to first conjugate and unbound second conjugate; and
   c) detecting the enzyme activity associated with either said solid phase or with said unbound second conjugate.

2. The method of claim 1 wherein said intrinsic factor molecules on said solid phase have parking areas of between about 30 and 400 angstroms$^2$ per intrinsic factor molecule.

3. The method of claim 1 wherein said first linking group is at least five angstroms long.

4. The method as recited in claim 1 wherein said second conjugate includes a cobalamin linked to a detectable enzyme with a second linking group at least three angstroms long.

5. The method as recited in claim 1 wherein said cobalamin is vitamin B12.

6. The method as recited in claim 5 wherein vitamin B12 is conjugated to said detectable enzyme through a group on the C ring of vitamin B12.

7. The method of claim 6 wherein vitamin B12 is carboxylated and converted to an amine at the 13 position on the C ring prior to linkage with said enzyme.

8. The method of claim 2 wherein said parking area is between about 200 and 400 angstroms$^2$/intrinsic factor molecule.

9. The method of claim 1 wherein said first conjugate is incubated with said sample to bind cobalamins in said sample, and further comprising washing said sample from said first conjugate prior to exposing said first conjugate and cobalamins to said second conjugate.

10. A kit for detecting cobalamins in a sample, comprising:
    a) a first conjugate of affinity purified intrinsic factor and a latex solid phase wherein said intrinsic factor and solid phase are linked together with a first linking group at least three angstroms long interposed between said solid phase and said intrinsic factor wherein said solid phase contains surface primary amine groups or surface primary carboxyl groups;
    b) a second conjugate of a cobalamin and a detectable enzyme.

11. The kit of claim 10 further including a wash solution for washing said sample from said first conjugate after said first conjugate has been incubated with said sample, but before said second conjugate has been added to the reaction mixture of said first conjugate and the cobalamins from the sample.

12. The kit of claim 10 wherein said second conjugate includes a second linking group at least five angstroms long between said cobalamin and detectable enzyme.

13. The kit of claim 10 wherein said cobalamin in said second conjugate is vitamin B12.

14. The kit of claim 13 said vitamin B12 is conjugated to said detectable enzyme through a group on the C ring of vitamin B12.

15. The kit of claim 14 wherein vitamin B12 is carboxylated and converted to an amine at the 13 position on the C ring prior to linkage with enzyme.

16. The kit of claim 10 wherein said intrinsic factor molecules on said solid phase have parking areas of between about 30 and 400 angstroms$^2$ per intrinsic factor molecule.

17. The kit of claim 16 wherein said parking distance is between about 200 and 400 angstroms$^2$/ intrinsic factor molecule.

18. The kit of claim 10 further including a substrate for said enzyme.

19. The kit of claim 10 wherein said affinity purified intrinsic factor comprises protein of which least 95% binds cobalamin.

20. A method for detecting cobalamins in a serum sample by performing an assay, comprising:
    combining to the sample a first conjugate of a latex solid phase linked to affinity purified intrinsic factor by a linking group at least three angstroms long and interposed between said solid phase and said intrinsic factor wherein said solid phase contains surface primary amine groups or surface primary carboxyl groups;

exposing said first conjugate and cobalamins from said sample to a second conjugate of a cobalamin linked to a detectable enzyme to produce second conjugate bound to said solid phase and unbound second conjugate; and detecting the enzyme activity associated with either said solid phase or said unbound second conjugate, wherein said assay has a detection limit of at least 150 pg/ml.

21. The method of claim 20 wherein said detection limit is about 60 pg/ml.

22. A conjugate comprising:

a latex solid phase linked to affinity purified intrinsic factor with a linking group of at least three angstroms in length interposed between said solid phase and said intrinsic factor wherein said solid phase has surface primary amine groups or surface primary carboxyl groups.

23. The conjugate of claim 22 wherein said intrinsic factor molecules on said solid phase have parking areas of between about 30 and 400 angstroms$^2$ per intrinsic factor molecule.

24. The conjugate of claim 23 wherein said parking distance is about 200 to about 400 angstroms$^2$ per intrinsic factor molecule.

25. The conjugate of claim 24 wherein said latex solid phase comprises microparticles.

26. The conjugate of claim 22 wherein said affinity purified intrinsic factor comprises protein of which at least 95% binds cobalamin.

* * * * *